(12) United States Patent
Abelson et al.

(10) Patent No.: US 11,246,483 B2
(45) Date of Patent: Feb. 15, 2022

(54) APPARATUS FOR CAPTURING AN IMAGE OF THE EYE

(71) Applicant: Ora, Inc., Andover, MA (US)

(72) Inventors: Richard Abelson, Gilbert, AZ (US); Mark B. Abelson, Teton Village, WY (US); Endri Angjeli, Quincy, MA (US); Keith Lane, Stow, MA (US)

(73) Assignee: Ora, Inc., Andover, MA (US)

( * ) Notice: Subject to any disclaimer, the term of this patent is extended or adjusted under 35 U.S.C. 154(b) by 0 days.

(21) Appl. No.: 15/837,712

(22) Filed: Dec. 11, 2017

(65) Prior Publication Data

US 2018/0160902 A1    Jun. 14, 2018

Related U.S. Application Data

(60) Provisional application No. 62/432,429, filed on Dec. 9, 2016.

(51) Int. Cl.
| | | |
|---|---|---|
| *A61B 3/14* | (2006.01) | |
| *G06K 9/00* | (2022.01) | |
| *G06T 7/00* | (2017.01) | |
| *H04N 5/225* | (2006.01) | |
| *G16H 30/20* | (2018.01) | |
| *A61B 3/00* | (2006.01) | |
| *G06F 16/51* | (2019.01) | |

(52) U.S. Cl.
CPC ............ *A61B 3/14* (2013.01); *G06K 9/00604* (2013.01); *G06T 7/0012* (2013.01); *H04N 5/2252* (2013.01); *A61B 3/0083* (2013.01); *G06F 16/51* (2019.01); *G06T 2207/30041* (2013.01); *G16H 30/20* (2018.01)

(58) Field of Classification Search
CPC ........... A61B 3/00; A61B 3/14; A61B 3/0083; H04N 5/2252; H04N 5/2251; G06K 9/00604; G06F 16/51; G16H 30/20; G06T 2207/30041; G06T 7/0012
See application file for complete search history.

(56) References Cited

U.S. PATENT DOCUMENTS

| | | | |
|---|---|---|---|
| 1,852,837 | A | 4/1932 | Daniel et al. |
| 1,859,756 | A | 5/1932 | Tillyer |
| 2,132,520 | A | 10/1938 | Taylor |
| 2,229,721 | A | 1/1941 | Brandt |
| D131,823 | S | 3/1942 | Peacock |
| D134,263 | S | 11/1942 | Derham |

(Continued)

FOREIGN PATENT DOCUMENTS

| | | |
|---|---|---|
| JP | 2004/065854 A | 3/2004 |
| JP | 2004/261316 A | 9/2004 |

(Continued)

*Primary Examiner* — Dave Czekaj
*Assistant Examiner* — Berteau Joisil
(74) *Attorney, Agent, or Firm* — Cooley LLP; Ivor R. Elrifi; Cynthia A. Kozakiewicz (57) ABSTRACT

The present invention relates to an apparatus including a base, a hollow receiving element joined to the base, and at least one positioning attachment that positions an imaging device received by the hollow receiving element to capture an image of at least one eye of a user. The present invention also relates to a method of capturing at least one image of at least one eye of a user using the above described apparatus.

26 Claims, 7 Drawing Sheets

(56) References Cited

U.S. PATENT DOCUMENTS

| | | |
|---|---|---|
| D153,847 S | 5/1949 | Bonilla |
| 2,826,194 A | 3/1958 | Seymour |
| 2,920,624 A | 1/1960 | Lerner |
| 3,016,898 A | 1/1962 | Erwin |
| 3,026,522 A | 3/1962 | Di Julio |
| 3,200,817 A | 8/1965 | Brainard |
| 3,279,466 A | 10/1966 | Mings |
| 3,314,426 A | 4/1967 | Albert |
| 3,602,217 A | 8/1971 | Felton et al. |
| 3,934,590 A | 1/1976 | Campagna et al. |
| D244,670 S | 6/1977 | Winikoff |
| 5,382,243 A | 1/1995 | Mulholland |
| D403,399 S | 12/1998 | Montgomery et al. |
| D413,668 S | 9/1999 | Mannberg et al. |
| D444,874 S | 7/2001 | Haffner et al. |
| D502,771 S | 3/2005 | Al Amri |
| D633,617 S | 3/2011 | Bricker et al. |
| 8,177,175 B2 | 5/2012 | Chang |
| D688,374 S | 8/2013 | Kweon |
| D694,402 S | 11/2013 | Lensch |
| D694,403 S | 11/2013 | Lensch |
| 8,746,638 B2 | 6/2014 | Carney |
| 8,798,453 B2 | 8/2014 | Lawton |
| D737,450 S | 8/2015 | Abelson |
| 9,131,132 B2 | 9/2015 | Graether |
| 9,436,222 B2 | 9/2016 | Lee et al. |
| D814,023 S | 3/2018 | Burgman |
| 2009/0109327 A1* | 4/2009 | Chen ............... G02B 7/02 348/374 |
| 2011/0085138 A1 | 4/2011 | Filar |
| 2014/0362283 A1 | 12/2014 | Coppage et al. |
| 2015/0381794 A1 | 12/2015 | Shulenberger |
| 2016/0051142 A1 | 2/2016 | Howes |
| 2016/0073877 A1* | 3/2016 | Su ............... A61B 50/31 351/206 |
| 2016/0073878 A1 | 3/2016 | Su et al. |
| 2016/0106369 A1 | 4/2016 | Yetik |
| 2016/0178112 A1 | 6/2016 | Shi et al. |
| 2016/0209733 A1* | 7/2016 | Akai ............... F16M 11/041 |
| 2016/0242734 A1 | 8/2016 | Su et al. |
| 2017/0367598 A1 | 12/2017 | Madsen |
| 2018/0153399 A1 | 6/2018 | Fink et al. |
| 2019/0191988 A1 | 6/2019 | Gargeya |
| 2019/0246986 A1 | 8/2019 | Rodger et al. |

FOREIGN PATENT DOCUMENTS

| | | |
|---|---|---|
| JP | 2005/094792 A | 4/2005 |
| JP | 3155214 U | 11/2009 |
| WO | WO-2012/176960 A1 | 12/2012 |
| WO | WO-2014/014168 A1 | 1/2014 |
| WO | WO-2015/054672 A1 | 4/2015 |

* cited by examiner

APPARATUS FOR CAPTURING AN IMAGE OF THE EYE

BACKGROUND OF THE INVENTION

The present disclosure relates to apparatuses and methods for capturing images of eyes utilizing an imaging device such as a smartphone. The captured images are used to study ocular diseases.

Patients may be afflicted with various ocular diseases including ocular conjunctivitis, blepharitis, dry eye disease, ocular redness or conjunctival hyperemia, eyelid swelling, and morning eyelid congestion (MEC) syndrome. Doctors, scientists, and other medical professionals continue to research treatments for these diseases. However, a large volume of images of patients' eyes are required to properly study these diseases.

For example, for some patients, ocular redness or eyelid swelling is a constant condition that does not show any diurnal variation. For other patients, redness or eyelid swelling appears individually and transiently. For other patients, both ocular redness and eyelid swelling appear together in the morning upon awakening and then subside over the morning (this condition is referred to as Morning Eyelid Congestion, MEC), and is transient, can be variable in severity and frequency (number of days it appears), and resolves over the course of the waking day, but is significant, and in cases even detrimental, from the perspective of their own subjective assessment and quality of life. The distinction between a persistent condition and one that is transient, resolving from morning through the day, may lead to different approaches for treatment. Proper capture of the severity and frequency of these conditions is needed and it is therefore important to properly characterize the profile of these patients with a transient condition (e.g. MEC) that consists of both swelling and redness, or either alone, because clinical assessment by a physician in the office may not properly capture the severity of transient conditions.

Useful images of the eyes must be precise, reproducible, and taken from a number of angles. In order to acquire images of the desired quality, current solutions require photographers to take images of patients' eyes in a controlled setting. This limits the number of times images can be taken and places a logistical and a financial burden on research into ocular disease.

The present disclosure provides improved apparatuses that pair with imaging devices to high quality images of the eye from any location. Methods of using the disclosed apparatuses are also provided.

SUMMARY OF THE INVENTION

According to certain embodiments, an apparatus is provided. The apparatus can include a base, a hollow receiving element joined to the base, and at least one positioning attachment. The receiving element can be configured to receive an imaging device. The at least one positioning attachment can be configured to position the imaging device to capture an image of at least one eye of a user.

According to certain embodiments, a method of capturing an image of at least one eye of a user is provided. The method can include inserting an imaging device in an apparatus. The apparatus can include a base, a hollow receiving element joined to the base, and at least one positioning attachment. The receiving element can be configured to receive an imaging device. The at least one positioning attachment can be configured to position the imaging device to capture an image of at least one eye of a user. The method can further include capturing at least one image of the at least one eye of the user.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Disclosed herein is an apparatus that enables individuals to capture images of their own eyes with an imaging device such as a smartphone.

Figure 1:
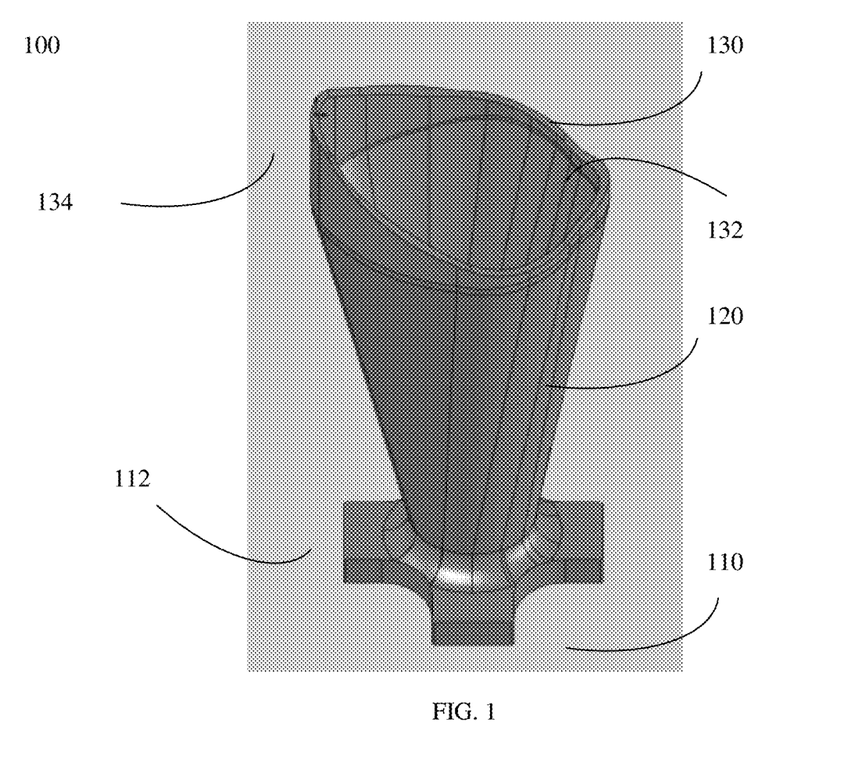
FIG. 1 is a perspective view of an apparatus for receiving an imaging device configured to capture a front image of a patient's eyes according to various exemplary embodiments.

FIG. 1 is a perspective view of an apparatus for receiving an imaging device to capture images of a patient's eyes according to various exemplary embodiments. The apparatus 100 includes a base 110 a hollow receiving element 120, and a positioning attachment 130. The apparatus 100 is configured to receive an imaging device and capture an image of at least one of a user's eyes.

The base 110 is configured to provide support and balance the apparatus 100. The base may include multiple extensions 112 extending radially from the center of the base 110. A base 110 with four extensions 112 is depicted in FIG. 1.

The base 110 is configured to join with a hollow element 120. In some embodiments, the base 110 and hollow element 120 are permanently joined, for example by soldering. In some embodiments, the base 110 and the hollow element 120 are removably joined. For example, the base 110 and the hollow element 120 may be joined by a fitted connection or magnetic connection.

The hollow element 120 is configured to receive an imaging device (not depicted). The imaging device may be any device capable of capturing images of sufficient quality for ocular disease research. In some embodiments, the imaging device is a smartphone, such as an iPhone®, Galaxy®, Droid®, and the like. In some embodiments, the hollow element 120 magnetically connects to the imaging device or a case around the imaging device.

The hollow element 120 is a sufficient depth and width to receive the imaging device. The hollow element 120 may be a depth ranging from 1 inch to 24 inches, or any depth in between such as 1, 2, 3, 4, 5, 6, 7, 8, 9, 10, 11, 12, 13, 14, 15, 16, 17, 18, 19, 20, 21, 22, 23, or 24 inches. The hollow element 120 may have a diameter ranging from 1 inch to 24 inches, or any diameter in between such as 1, 2, 3, 4, 5, 6, 7, 8, 9, 10, 11, 12, 13, 14, 15, 16, 17, 18, 19, 20, 21, 22, 23, or 24 inches. In some embodiments, the hollow element is adjustable and extendible.

The positioning attachment 130 is configured to position the imaging device within the apparatus 100 to enable a photo of a user's eyes from a front view. The positioning attachment 130 is removably joined to the hollow element 120. For example, the positioning attachment 130 and the hollow element 120 may be joined by a fitted connection or magnetic connection.

The positioning attachment 130 is substantially circular and has first portion 132 and a second portion 134. The first portion 132 is shorter than the second portion 130. The first portion 132 is positioned in front of a camera of the imaging device. The second portion 134 is positioned on the opposite side of the camera of the imaging device. The second portion 134 is of sufficient height to support the imaging device and prevent movement of the imaging device while in use.

The first portion 132 may have a height ranging from 1 inch to 24 inches, or any height in between such as 1, 2, 3, 4, 5, 6, 7, 8, 9, 10, 11, 12, 13, 14, 15, 16, 17, 18, 19, 20, 21, 22, 23, or 24 inches. The second portion 134 may have a height ranging from 1 inch to 24 inches, or any height in between such as 1, 2, 3, 4, 5, 6, 7, 8, 9, 10, 11, 12, 13, 14, 15, 16, 17, 18, 19, 20, 21, 22, 23, or 24 inches. The positioning attachment 130 may have a diameter ranging from 1 inch to 24 inches, or any diameter in between such as 1, 2, 3, 4, 5, 6, 7, 8, 9, 10, 11, 12, 13, 14, 15, 16, 17, 18, 19, 20, 21, 22, 23, or 24 inches.

Figure 2:
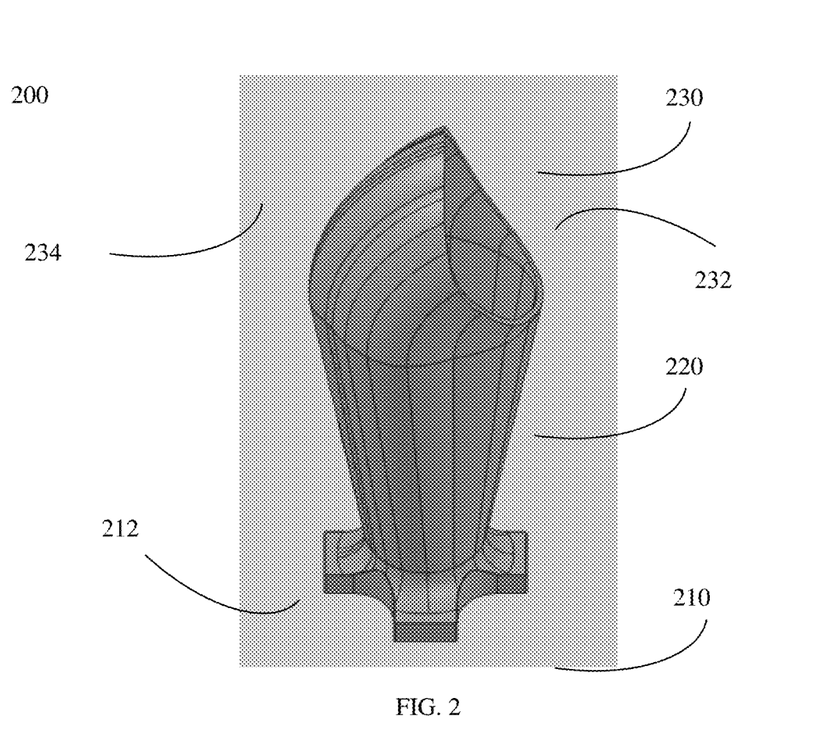
FIG. 2 is a perspective view of the apparatus for receiving an imaging device configured to capture 90° temporal side image of a patient's eyes according to various exemplary embodiments.

FIG. 2 is a perspective view of the apparatus for receiving an imaging device to capture a 90° temporal side image of at least one of a patient's eyes according to various exemplary embodiments. The apparatus 200 includes a base 210, a hollow receiving element 220, and a positioning attachment 230.

The apparatus 200 is similar to that of apparatus 100 except the positioning attachment 230 is configured to position an imaging device to capture a 90° temporal side image of at least one of a patient's eyes. The positioning attachment 230 has a first portion 232 and a second portion 234. The first portion 132 is shorter than the second portion 130. The first portion 132 is positioned in front of a camera of the imaging device. The second portion 134 is positioned on the opposite side of the camera of the imaging device but may extend over or beyond the center of the imaging device towards the camera side of the imaging device.

The first portion 132 may have a height ranging from 1 inch to 24 inches, or any height in between such as 1, 2, 3, 4, 5, 6, 7, 8, 9, 10, 11, 12, 13, 14, 15, 16, 17, 18, 19, 20, 21, 22, 23, or 24 inches. The second portion 134 may have a height ranging from 1 inch to 24 inches, or any height in between such as 1, 2, 3, 4, 5, 6, 7, 8, 9, 10, 11, 12, 13, 14, 15, 16, 17, 18, 19, 20, 21, 22, 23, or 24 inches. The positioning attachment 130 may have a diameter ranging from 1 inch to 24 inches, or any diameter in between such as 1, 2, 3, 4, 5, 6, 7, 8, 9, 10, 11, 12, 13, 14, 15, 16, 17, 18, 19, 20, 21, 22, 23, or 24 inches.

The portion of the positioning attachment 230 including the second portion 234 may extend medially towards the center of the apparatus 200 at an angle. The angle may range from 1 degree to 90 degrees, or any degree in between. In an embodiment, the angle is 90°.

In some embodiments, the imaging device is a smartphone. The smartphone may include an application designed to instruct a user through an imaging process. The application may include directions on how to assemble the device and how to place the smartphone within the apparatus. The application may also utilize the smartphone's camera directly and include optimal parameters for capturing images. Such optimal parameters may be brightness, strength of flash, number of pixels, filters, and the like. In some embodiments, the application transmits captured images to a database for review by scientists and/or medical professionals.

Figure 3:
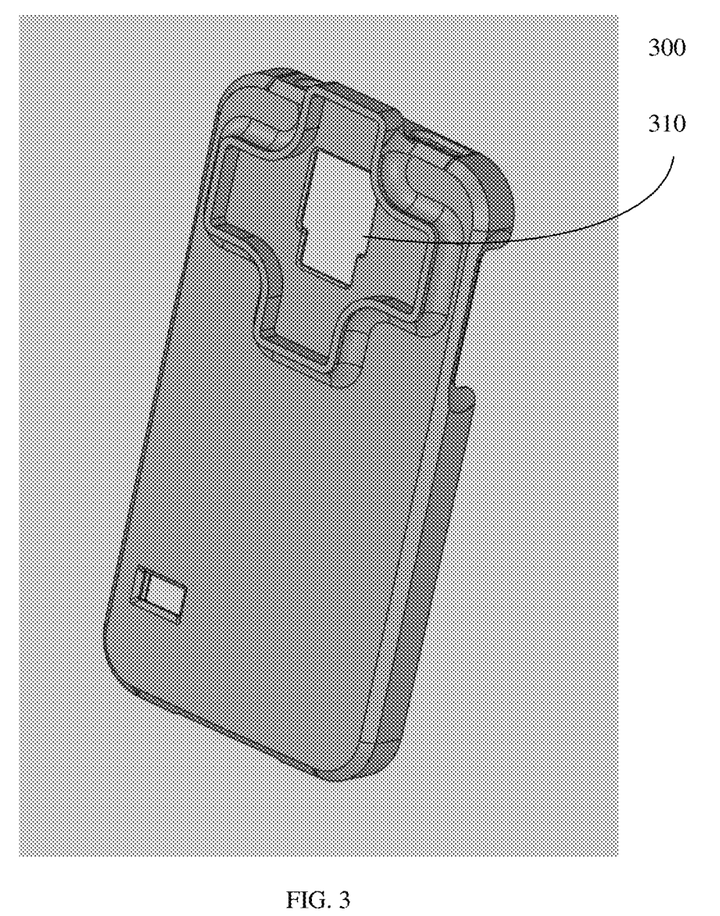
FIG. 3 is a perspective view of a case for an imaging device according to various exemplary embodiments.

FIG. 3 is a perspective view of a case for an imaging device according to various exemplary embodiments. The case 300 is sized to snugly fit around an imaging device (not shown). In some embodiments, the imaging device is a smartphone, such as an iPhone®, Galaxy®, Droid®, and the like. Magnets may be located throughout, within, or attached to the case 300.

The case 300 is configured to be inserted within a hollow element of an apparatus. The case 300 may be removably secured within the hollow element. In some embodiments, the case 300 is magnetically connected to the hollow element. The position of the case 300 is adjustable and may be determined by a positioning attachment of the apparatus.

The case 300 includes at least one aperture 310 to provide an opening for a camera of the imaging device. The aperture 310 is located within the case 300 relative to the imaging device the case 300 is designed for. As a non-limiting example, a case 300 for a Samsung Galaxy S5® would include an aperture 310 along the center longitudinal axis of the case 300 near the top lateral edge of the case 300.

Figure 4:
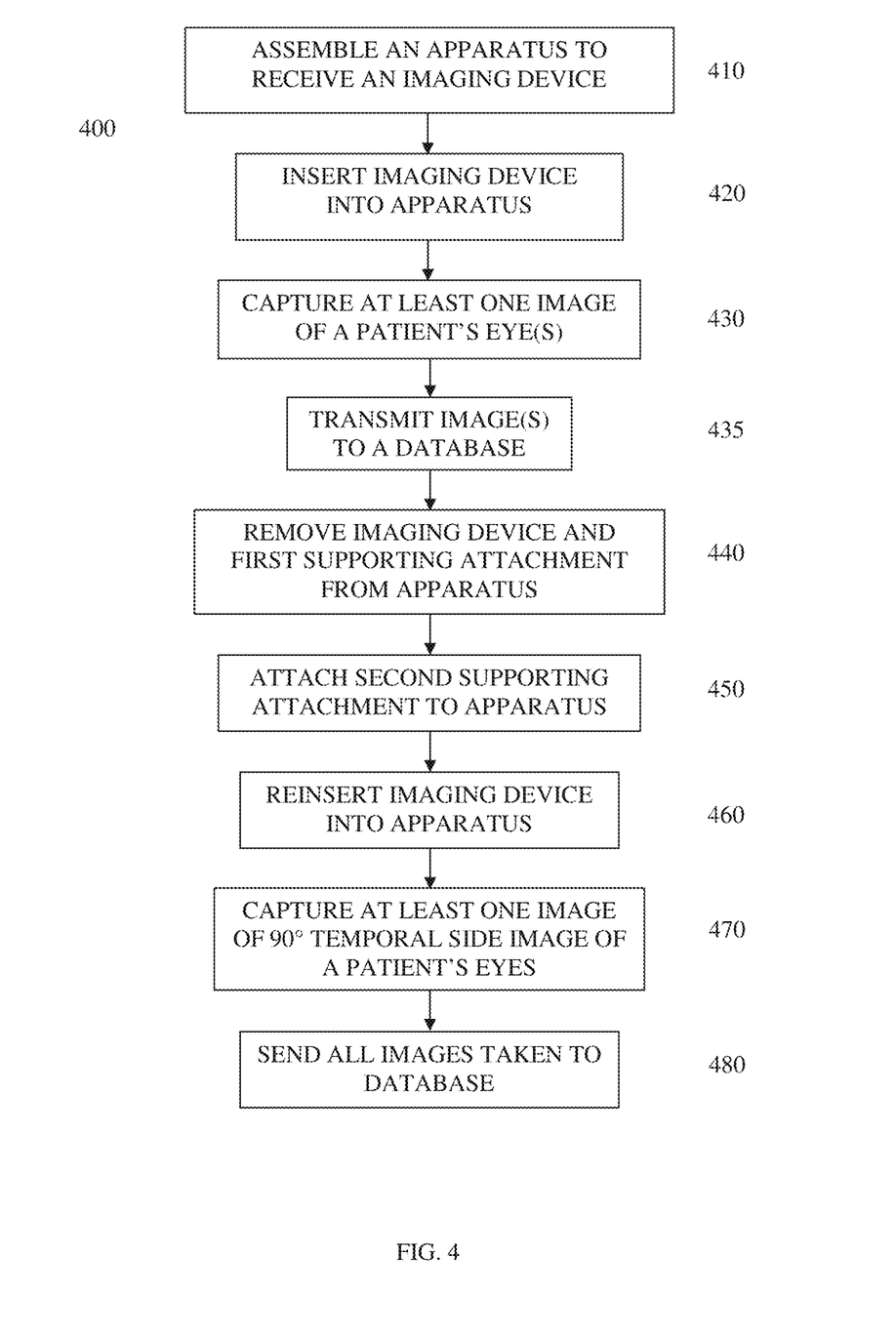
FIG. 4 depicts a method of capturing images of a patient's eye(s) according to various exemplary embodiments.

FIG. 4 depicts a method 400 of capturing images of a patient's eye(s). The method may be performed by the patient or by another user. The method begins at step 410 when an apparatus is assembled to receive an imaging device. Then, at step 420 an imaging device is inserted into the apparatus. The imaging device may be secured via physical contact with the apparatus. In some embodiments, the imaging device is a smartphone.

Next at step 430 at least one image of a patient's eye(s) is captured by the imaging device. The at least one image may be a front image of the patient's eye(s), a fixed-perspective image of the peri-ocular region, or other image of at least one eye. The at least one image allows clinicians to evaluate the subjective assessments of swelling provided by patients while providing a system and method for controlled, repeatable, at-home imaging that could be used for clinician confirmation of a condition. The subjective assessments can be recorded in a patient diary. The subjective assessments can include patient comfort, quality of life, and the like. In some embodiments, the patient diary can be recorded in the imaging device. The patient diary can be set with reminders to ensure compliance of recording the subjective assessments, dosing of drugs (if applicable) and other notices. At optional step 435, the at least one image may be transmitted to a database after the at least one image is taken.

Then at step 440 the imaging device and a first supporting attachment of the apparatus are removed from the apparatus. Next at step 450 a second supporting attachment is attached to the apparatus. The first supporting attachment may be configured to position the imaging device to capture a front image of at least one of a patient's eyes. The second supporting attachment may be configured to position the imaging device to capture a 90° temporal side image of at least one of a patient's eyes.

After the second supporting attachment is attached, at step 460 the imaging device is reinserted into the apparatus. Then at step 470 at least one image of 90° temporal side image of at least one of a patient's eyes is captured. The method concludes at step 480 when all images taken are sent to a database for review by scientists, clinicians, and/or medical professionals.

EXAMPLE 1

Example 1 describes a single-center, three-week study evaluating the frequency, severity, and duration of morning eyelid congestion in an environmental setting using the at-home electronic diary and eyelid image capture system. All subjects were 18 years of age or older, provided informed consent, and were willing and able to follow all instructions. Slit lamp biomicroscopy examinations and visual acuity assessments were conducted at each study visit. Subjects for the study were required to satisfy inclusion criteria at both baseline (Visit 1) and following a 6-day screening period (Visit 2).

To satisfy inclusion criteria at Visit 1, all subjects were required to self-report morning eyelid congestion (i.e. both conjunctival redness and eyelid swelling) that (1) lasted for at least 2 hours after waking, (2) had occurred at least 3 days in the prior week and (3) had an in-office, retrospective subjective grade of eyelid edema of at least 3 (on a 0-4 scale) upon awakening, on at least one day. Exclusion criteria included active ocular infection or inflammation, active blepharitis, meibomian gland dysfunction, ocular allergies that required therapeutic treatment, marked facial asymmetry, ptosis, significant dermatochalasis, deep dermal scarring, history of facial nerve palsy, prior blepharoplasty, use of any cosmetics marketed for reduction of eyelid swelling, history of ocular surgical procedure within 12 months, and use of any topical ocular medications within 24 hours prior to Visit 1 or for the duration of the study other than artificial tear substitutes. In addition, subjects with any uncontrolled systemic disease, or any condition that, in the opinion of the investigator, could confound the study results were also excluded.

Subjects satisfying entry criteria were provided the disclosed apparatus. They were asked to capture lid images (1 image from front and 1 image from temporal side for each eye) and grade their eyelid swelling and conjunctival redness (0-4 scale) during the evening, upon waking, 30 minutes after waking, and at 1, 2, 3, 4, 5, and 6 hours after waking for the next six days.

All subjects at Visit 2 were required to demonstrate each of the following: (1) at least 1 day of eyelid swelling in the diary graded as a 3 or higher in at least one eye; (2) at least 1 day of eyelid swelling in the diary that resolved 2 or more hours after awakening; (3) at least one episode of clinician-verified present lid swelling (as recorded in diary and in images reviewed by the physician) corresponding to a grade of ≥2 (0-4 scale). Subjects satisfying inclusion criteria at Visit 2 proceeded in the study and used the disclosed apparatus for an additional 14 days, capturing lid images and grading their eyelid swelling and conjunctival redness (0-4 scale) in a similar manner (evening, upon waking, 30 minutes after waking, and at 1, 2, 3, 4, 5, and 6 hours after waking).

Primary evaluation measures were subject-graded global eyelid swelling (on a 0 to 4 scale in which 0=no lid swelling and 4=severe lid swelling) and conjunctival redness (0 to 4 scale, with 0=no redness and 4=severe redness). Secondary measures included subject-graded regional eyelid swelling (0-4 scale per region) and a lid swelling questionnaire. Safety measures included adverse event query, best-corrected visual acuity, and slit lamp biomicroscopy. Symptoms were evaluated with a lid swelling questionnaire, a lid swelling scale, and conjunctival redness scale using the Ora Calibra™ scales.

At home, subjects used a diary system to capture two photographs of each eye, and to evaluate symptoms the prior evening, upon awakening, after 30 minutes, and hourly from 1 to 6 hours after awakening using the same grading systems described above for the screening period.

A total of 29 subjects satisfied inclusion criteria at Visit 1 and were provided an electronic diary and the disclosed apparatus for the 6-day screening period. At Visit 2 (Day 7±2), the subject's diary recordings were reviewed. A total of 22 of the 29 subjects satisfied inclusion criteria at Visit 2 and proceeded to Visit 3 (Day 21±2). Of those subjects who were discontinued at Visit 2, two were unable or unwilling to use the disclosed apparatus, two were judged by clinicians to not have lid swelling based on the diary images, and three did not report at least 1 day with swelling score of sufficient severity. The screening process demonstrates the utility of using the eyelid image capturing and diary system to capture images and subjective assessment that can be reviewed by a clinician at an office visit.

Figure 5:
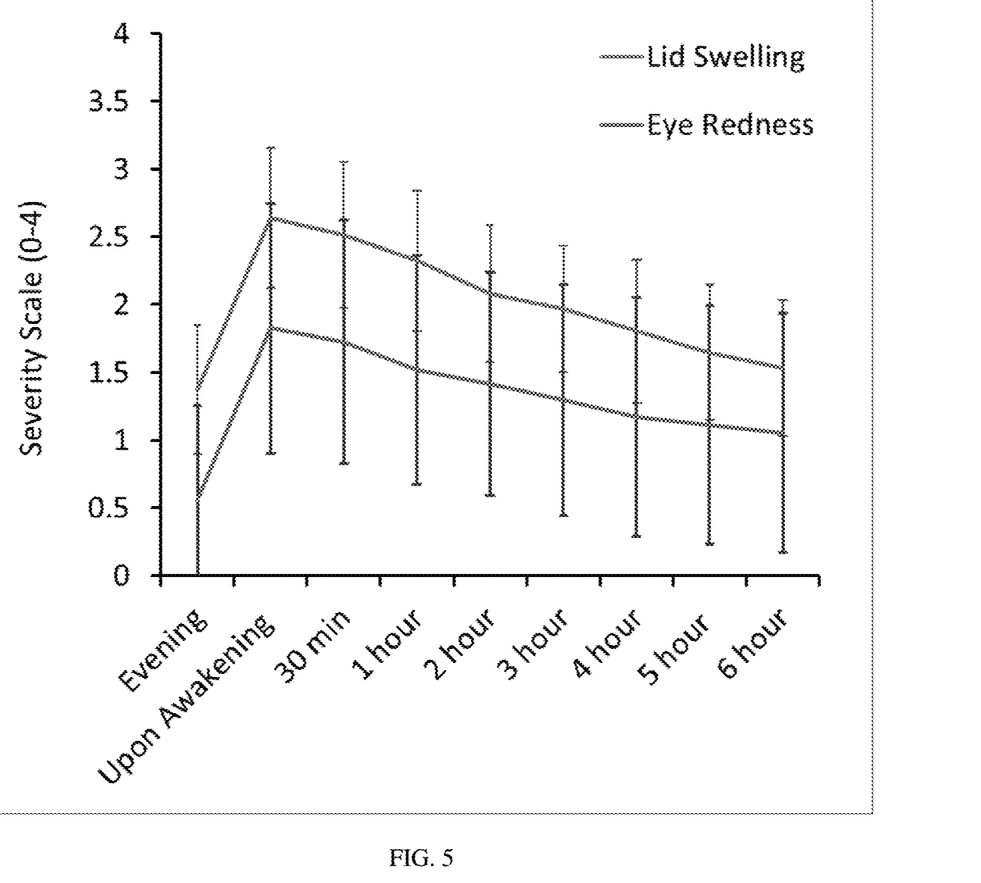
FIG. 5 is a graph illustrating mean lid swelling and redness values recorded from subjects in Example 1, as captured by the disclosed apparatus.

The mean lid swelling values recorded from the subjects are illustrated in FIG. 5. The mean lid swelling scores upon awakening for all 22 subjects over the 20 days of observation was 2.64±0.55. The mean lid swelling score at evening was 1.44±0.65; the mean lid swelling scores at 6 hours post awakening was 1.53±0.49, similar to the evening scores.

Of the 22 subjects enrolled, 19 (86.4%) demonstrated a pattern of transient lid swelling that improved steadily in the 1-6 hours after awakening. In these 19 individuals, morning lid swelling was observed on the majority (mean of 15±4 days) of the 20 days of observation. In 3 subjects, lid swelling of similar severity remained present for the entire 6 hour observation window.

As seen in FIG. 5, the conjunctival redness scores followed a pattern similar to that of lid swelling. The scores were maximal upon waking, with a mean of 1.83±0.97. The lowest scores for redness were observed in the evening, with a mean of 0.51±0.65. The mean conjunctival redness score at 6 hours post awakening was 1.05±0.94. Seventeen (77.3%) of the 22 enrolled subjects showed a transient conjunctival redness that improved within 1-6 hours of awakening. Among these subjects, this transient redness was reported on most days (mean of 12±8 days) over the course of the 20-day study. In the remaining 5 subjects, 2 did not exhibit redness and 3 had persistent redness throughout the 6 hour observation period post-awakening.

Overall, 16 (72.7%) of 22 subjects exhibited both eyelid swelling and redness which peaked upon wakening and slowly resolved over the course of 1-6 hours. This subgroup of 16 subjects satisfied the criteria defined for the condition of morning eyelid congestion (MEC).

Figure 6:
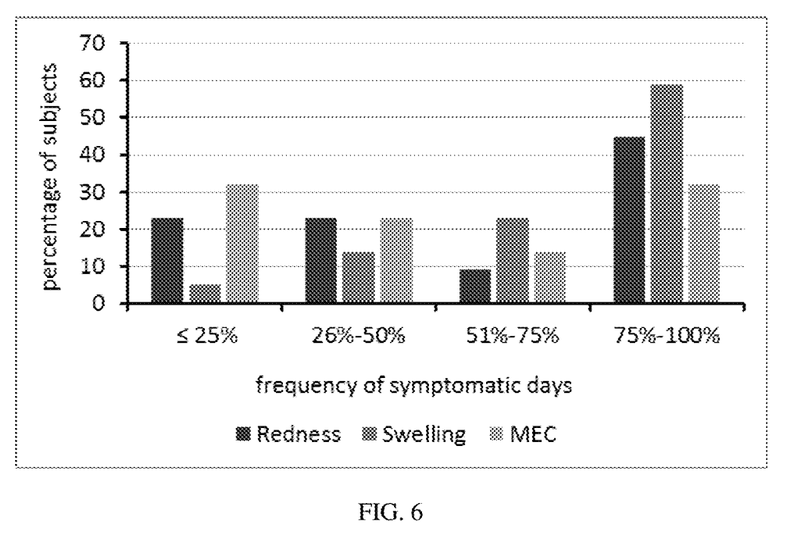
FIG. 6 is a chart depicting the percentage of days that subjects in Example 1 experienced lid swelling, conjunctival redness, or both, as captured by the disclosed apparatus.

A notable feature of MEC is its sporadic nature. FIG. 6 shows the percentage of days (from a total of 20 study days) that subjects experienced lid swelling, conjunctival redness, or both. Day-to-day variability was evident between subjects, with MEC present in approximately a third of subjects on at least 75% of days during the study.

Figure 7:
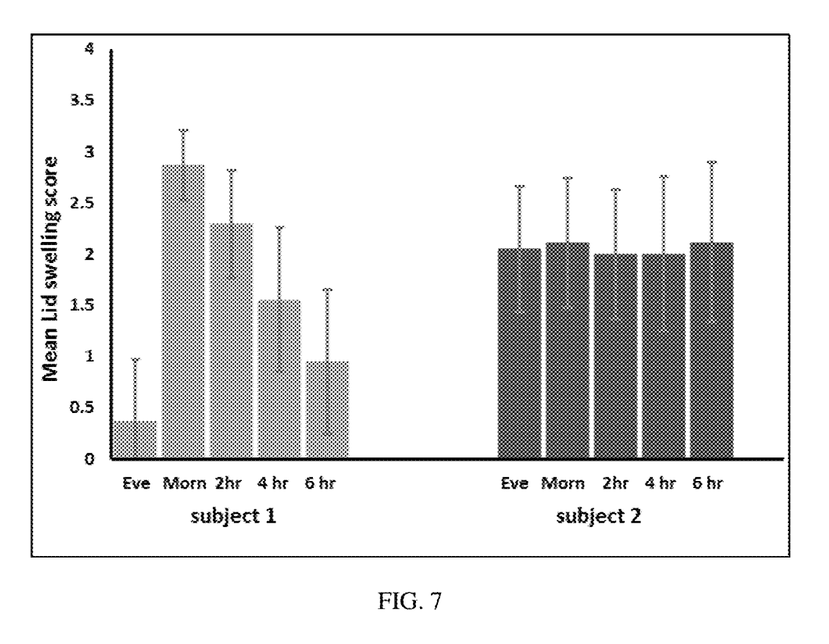
FIG. 7 depicts lid swelling data of two subjects in Example 1 as captured by the disclosed apparatus.

Among those individuals who self-identified with MEC, the overwhelming majority (86.4%) of subjects demonstrated a pattern of transient symptomatology over the course of the waking hours. In addition, 3 subjects (13.6%) who self-reported lid swelling had a persistent lid swelling which was similar in severity across evening, upon awakening, and over the course of the first 6 waking hours. In contrast, the majority of the study population displayed the pattern of decreased swelling and hyperemia over the course of the day. Lid swelling patterns of two subjects with different patterns are depicted in FIG. 7.

A quality of life survey of subjects who had self-identified as experiencing some degree of MEC was also conducted to assess subjective aspects of the condition. The results of the survey are depicted in Table 1.

TABLE 1

|  | Yes | No |
|---|---|---|
| Has your eyelid swelling or eyelid puffiness ever caused you to apply make-up? | 57% | 43% |
| Has your eyelid swelling or eyelid puffiness ever caused a loss in self-confidence? | 47% | 53% |
| Has your eyelid swelling or eyelid puffiness ever impacted your daily routine? | 23% | 77% |
| Has your eyelid swelling or eyelid puffiness ever caused an increase in time to get ready in the morning? | 63% | 37% |
| When does eyelid swelling occur? | 37% | Everyday |
|  | 53% | Most Days |
|  | 10% | Some Days |
|  | 0% | Never |

A high percentage of subjects (90%) reported that they suffered MEC "everyday" or "most days". In addition, a majority of respondents reported that their MEC impacted daily routines such as morning preparation times (63%).

The study provides the basis for identification of a well-defined population of individuals who experience MEC: a transient, self-resolving edema of the peri-ocular region in combination with a mild to moderate conjunctival hyperemia. A majority of those in the study (73%) who experience a morning eyelid swelling have MEC, while others (14%) experience a separate, more persistent condition likely due to a distinct set of underlying factors. In addition, the successful application of the disclosed apparatus provided the tools necessary to assess MEC, and any potential treatments that may provide therapeutic benefit for MEC, in a well-designed, controlled study.

The objective of this study was to refine the methods used to characterize MEC in the hope that a distinct population (or populations) of subjects report this condition could be identified based upon a shared symptomology. Two distinct populations have been distinguished along with a set of endpoints that allows clinicians to further characterize and properly select those to treat with MEC based on data captured with the disclosed apparatus.

In the study, roughly three quarters (16/22; 72.7%) of the subjects who self-reported MEC observed gradable lid swelling and redness at 2 or more days over a 20 day observation period. In these subjects, most experienced MEC sporadically. This finding suggests that even in a self-defined population who suffers from this condition, MEC presents only sporadically in most subjects. This point emphasizes the importance of extended periods of observation when attempting to study and profile the frequency and severity of MEC experienced by each individual. Furthermore, the presence of both redness and swelling in the majority of this population suggests that both are essential diagnostic criteria.

Individuals recruited for this study were all self-reported as experiencing the combination of frequent eyelid puffiness and conjunctival redness upon awakening. The impact of this condition was explored in a brief quality of life survey, in which subjects report a disruption of morning routines and an impact on attitudes regarding personal appearance; for these individuals, 90% report that they experience MEC all or most mornings. These numbers reflect the impact that MEC has on subjects' self-image, since the data suggest that measurable MEC occurs for this group about 50% of the time. This initial assessment suggests that treatments to reduce severity or frequency of MEC in those susceptible to it would have a substantial, positive impact on quality of life and self-image. It also demonstrates the importance of proper characterization of these patient populations to properly identify those that report and exhibit significant eyelid swelling and redness (morning eyelid congestion-MEC). The characterization and definition of the condition presented here provides important guidance in future efforts to develop such treatments. In particular, characterization of the MEC condition in this study was driven by the ability to collect data from an at-home diary based electronic system that supports patient compliance and facilitated data collection of both subjective scoring as well as images that were used by physicians to confirm presence of the condition for enrollment. This study also demonstrated that even in patients who report redness and swelling, not all have a verified condition. Further, the eyelid image capturing system was able to properly capture an actual frequency and severity and identify patients who have MEC, which is both redness and swelling together that is transient.

What is claimed is:

1. An apparatus to capture images of an eye and periocular region of a user comprising: a hollow base, a hollow receiving element, and a hollow positioning attachment, wherein
    the hollow base is configured to join an imaging device to the hollow receiving element;
    the hollow receiving element is configured to join the hollow base to the hollow positioning attachment; and
    the hollow positioning attachment is contoured to conform to the face of the user and position the imaging device to capture an image of the eye and periocular region of the user at a desired angle relative to the front view of the face of the user.

2. The apparatus of claim 1, wherein the base comprises at least one extension extending radially from a center of the hollow base.

3. The apparatus of claim 2, wherein the hollow base comprises four extensions.

4. The apparatus of claim 1, wherein the hollow base is configured to connect a case to secure the imaging device.

5. The apparatus of claim 1, wherein the hollow positioning attachment is configured to position the imaging device to capture a front image of the eye and peri-ocular region of the user.

6. The apparatus of claim 1, wherein the hollow positioning attachment is configured to position the imaging device capture a 90° temporal side image of the eye and peri-ocular region of the user.

7. A method of capturing an image of an eye and the peri-ocular region of a user, comprising:
inserting an imaging device in an apparatus, the apparatus comprising: a hollow base, a hollow receiving element, and a first hollow positioning element, wherein
the hollow base is configured to join the imaging device to the hollow receiving element;
the hollow receiving element is configured to join the hollow base to the first hollow positioning attachment; and
the hollow positioning attachment is contoured to conform to the face of the user and position the imaging device at a desired angle relative to the front view of the face of the user; and
capturing at least one image of the eye and peri-ocular region of the user.

8. The method of claim 7, further comprising transmitting the at least one captured image to a database.

9. The method of claim 8, further comprising replacing the first hollow positioning attachment with a second hollow positioning attachment configured to position the imaging device to capture a 90° temporal side image of the eye of the user.

10. The method of claim 9, wherein the hollow base comprises at least one extension extending radially from a center of the base.

11. The method of claim 10, wherein the hollow base comprises four extensions.

12. The method of claim 11, wherein the imaging device is a smartphone.

13. The apparatus of claim 6, wherein the imaging device is a smartphone.

14. The apparatus of claim 13, wherein the hollow base and the hollow receiving element are permanently joined.

15. The apparatus of claim 13, wherein the hollow base and the hollow receiving element are joined by a removable connection, wherein the removable connection is a magnetic or fitted connection.

16. The apparatus of claim 14 or 15, wherein the hollow receiving element is a sufficient depth and width to receive the imaging device.

17. The apparatus of claim 16, wherein the hollow receiving element has a depth ranging from 1 inch to 24 inches and a diameter ranging from 1 inch to 24 inches.

18. The apparatus of claim 17, wherein the hollow positioning attachment joins the hollow receiving element by a fitted or magnetic connection.

19. The apparatus of claim 18 wherein the hollow positioning attachment is substantially circular and has a first portion and a second portion.

20. The method of claim 11, wherein the hollow base is configured to connect a case to secure the imaging device.

21. The method of claim 20, wherein the hollow base and the hollow receiving element are permanently joined.

22. The method of claim 20, wherein the hollow base and the hollow receiving element are joined by a removable connection, wherein the removable connection is a magnetic or fitted connection.

23. The method of claim 21 or 22, wherein the hollow receiving element is a sufficient depth and width to receive the imaging device.

24. The method of claim 23, wherein the hollow receiving element has a depth ranging from 1 inch to 24 inches and a diameter ranging from 1 inch to 24 inches.

25. The method of claim 24, wherein the hollow positioning attachment joins the hollow receiving element by a fitted or magnetic connection.

26. The method of claim 25, wherein the hollow positioning attachment is substantially circular and has a first portion and a second portion.

* * * * *